US008168790B2

(12) United States Patent
Bao et al.

(10) Patent No.: US 8,168,790 B2
(45) Date of Patent: May 1, 2012

(54) PROCESS FOR THE PREPARATION OF 6-BETA HYDROXY MORPHINAN COMPOUNDS

(75) Inventors: Jian Bao, Chesterfield, MO (US); Tao Jiang, St. Louis, MO (US); Gary L. Cantrell, Troy, IL (US)

(73) Assignee: Mallinckrodt LLC, Hazelwood, MO (US)

( * ) Notice: Subject to any disclaimer, the term of this patent is extended or adjusted under 35 U.S.C. 154(b) by 402 days.

(21) Appl. No.: 12/485,200

(22) Filed: Jun. 16, 2009

(65) Prior Publication Data
US 2009/0312552 A1    Dec. 17, 2009

Related U.S. Application Data

(60) Provisional application No. 61/073,076, filed on Jun. 17, 2008.

(51) Int. Cl.
*C07D 489/02*    (2006.01)
*C07D 489/08*    (2006.01)
(52) U.S. Cl. .......................................... 546/44; 546/45
(58) Field of Classification Search .................... 546/46, 546/45, 44
See application file for complete search history.

(56) References Cited

U.S. PATENT DOCUMENTS
4,912,114 A    3/1990 Revesz

FOREIGN PATENT DOCUMENTS
WO    WO 2007/124114    11/2007
WO    WO 2008/070462    6/2008

OTHER PUBLICATIONS

Uwai et al., "Syntheses and receptor-binding studies of derivatives of the opioid antagonist naltrexone", Bioorganic & Medicinal Chemistry, 2004, 12, pp. 417-421 XP002499242.
Kalinin et al., "Palladium-catalyzed 2-phenylethenylation of codeine: 8-[(1E)-2-phenylethenyl]codeinone dimethyl ketal as the unexpected 'masked' diene for the preparation of 19-substituted Diels-Alder adducts of thebaine", Helvetica chimica Acta, 2006, vol. 89, No. 5, 2006, pp. 861-869 XP002538221.
Olofson et al., "A new reagent for the selective, high-yield N-dealkylation of tertiary amines: Improved syntheses of Naltrexone and nalbuphine", Journal of Organic Chemistry, 1984, vol. 49, No. 11, pp. 2081-2082 XP002538222.
Hamad et al., "Synthesis and hydrolytic behavior of two novel tripartite codrugs of Naltrexone and 6beta-naltrexol with hydroxybupropion as potential alcohol abuse and smoking cessation agents", Bioorganic & Medicinal Chemistry, vol. 14, No. 20, 2006, pp. 7051-7061 XP025133617.
Chatterjie et al., "Stereospecific synthesis of the 6beta-hydroxy metabolites of Naltrexone and naloxone", Journal of Medicinal Chemistry, 1975, vol. 18, No. 5, pp. 490-492 XP002538223.
Kayakiri et al., "Probes for narcotic receptor mediated phenomena. 24. synthesis, single crystal X-ray analyses, in vitro and in vivo properties of 6alpha-and 6beta-IODO-3,14-dihydroxy-17methyl-4,5alpha-epoxymorphinans", Medicinal Chemistry Research, 1996, vol. 6, pp. 427-438 XP008108680.
Chatterjie et al., "Stereospecific Synthesis of the 6b-hydroxy Metabolites of Naltrexone and Naloxone", Journal of Medicinal chemistry, 1975, 18(5), pts. 490-492.
Brine et al., "Formamidinesulfinic Acid Reduction of Dihydrocodeinone Derivatives", Journal of Organic Chemistry, 1978, 43(8), pp. 1555-15557.

*Primary Examiner* — Charanjit Aulakh

(57) ABSTRACT

The invention provides processes for the conversion of a 6-keto morphinan to a 6-hydroxy morphinan. In particular, the invention provides a stereoselective process for the conversion of a 6-keto morphinan to a 6-beta-hydroxy morphinan.

11 Claims, No Drawings

PROCESS FOR THE PREPARATION OF 6-BETA HYDROXY MORPHINAN COMPOUNDS

CROSS-REFERENCE TO RELATED APPLICATIONS

This application claims priority from Provisional Application Ser. No. 61/073,076 filed on Jun. 17, 2008, which is hereby incorporated by reference in its entirety.

FIELD OF THE INVENTION

The present invention generally relates to processes for the conversion of a 6-keto morphinan to a 6-hydroxy morphinan. In particular, the invention provides a stereoselective process for the conversion of a 6-keto morphinan to a 6-beta-hydroxy morphinan.

BACKGROUND OF THE INVENTION

The stereoselective reduction of the 6-keto group of certain morphinan compounds is a necessary step in the preparation of many opiate-based compounds. For example, 6-beta-hydroxy morphinan derivatives have valuable medical potential for the unmet needs of pain management and addiction therapy. Traditionally, a 6-beta-hydroxy epimer has been prepared by reducing the corresponding 6-keto compound in a large volume of an alkaline solution of formamidine sulfinic acid. Not only are the yields of the reaction low, but the reaction also generates large volumes of caustic waste material. If the reaction is run in a more concentrated environment, however, one of the components precipitates out of solution and the reaction stalls prior to completion. As a consequence, the resulting 6-hydroxy morphinan product is contaminated with large amounts of the unconverted starting material. Accordingly, a need exists for an efficient and scalable process for converting 6-keto-morphinans to 6-beta-hydroxy morphinans in pharmaceutical grade quality. The process should ensure high yield, high epimeric purity, and simple isolation of the desired compound.

SUMMARY OF THE INVENTION

Among the various aspects of the present invention is a provision of a process for the conversion of a 6-keto morphinan compound comprising Formula (I) to a 6-beta-hydroxy morphinan compound comprising Formula (II). The process comprises two sequential steps. The first step comprises contacting compound (I) with a reducing agent and a first proton acceptor to form a first homogeneous reaction mixture, wherein some of compound (I) is converted to compound (II) to produce a substantially heterogeneous reaction mixture. The second step comprises contacting the heterogeneous reaction mixture with a second proton acceptor to form a second homogeneous reaction mixture, wherein some of compound (i) that was not converted to compound (II) in step (a) is converted to compound (II). The following reaction scheme depicts steps (a) and (b) of the process:

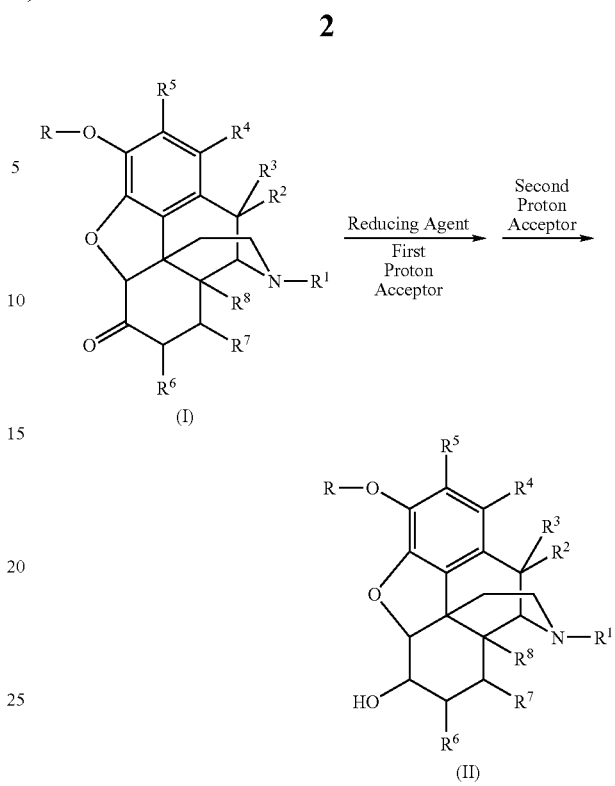

wherein:

R is selected from the group consisting of hydrogen, hydrocarbyl, substituted hydrocarbyl, and hydroxy protecting group $R^1$ is selected from the group consisting of hydrogen, hydrocarbyl, and substituted hydrocarbyl;

$R^2$ and $R^3$ are independently selected from the group consisting of hydrogen, OH, $NH_2$, SH, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group selected from the group consisting of cycloalkyl ketal, cycloalkyl thiol ketal, and cycloalkyl dithiol ketal;

$R^4$, $R^5$, $R^6$, and $R^7$ are independently selected from the group consisting of hydrogen, halogen, $NH_2$, CN, SH, $CF_3$, $OR^9$, hydrocarbyl, and substituted hydrocarbyl;

$R^8$ is selected from the group consisting of hydrogen and hydroxy; and $R^9$ is selected from the group consisting of hydrogen, hydrocarbyl, substituted hydrocarbyl, and hydroxy protecting group.

Another aspect of the present invention encompasses a process for the conversion of a 6-keto morphinan compound comprising Formula (III) to a 6-hydroxy morphinan compound comprising Formula (IV). The first step of the process comprises contacting compound (III) with a reducing agent and a first proton acceptor to form a first homogeneous reaction mixture, wherein some of compound (III) is converted to compound (IV) to form a substantially heterogeneous reaction mixture. The second step of the process comprises contacting the heterogeneous reaction mixture with a second proton acceptor to form a second homogeneous reaction mixture, wherein some of compound (III) that was not converted to compound (IV) in step (a) is converted to compound (IV).

The following reaction scheme depicts steps (a) and (b) of the process:

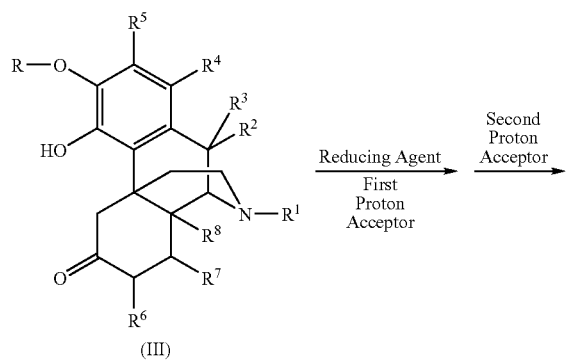

(III)

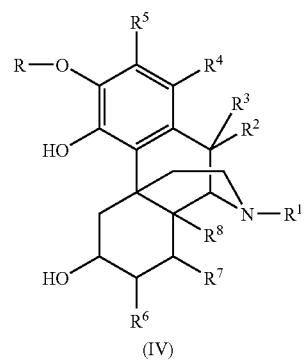

(IV)

wherein:
R is selected from the group consisting of hydrogen, hydrocarbyl, substituted hydrocarbyl, and hydroxy protecting group
$R^1$ is selected from the group consisting of hydrogen, hydrocarbyl, and substituted hydrocarbyl;
$R^2$ and $R^3$ are independently selected from the group consisting of hydrogen, OH, $NH_2$, SH, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group selected from the group consisting of cycloalkyl ketal, cycloalkyl thiol ketal, and cycloalkyl dithiol ketal;
$R^4$, $R^5$, $R^6$, and $R^7$ are independently selected from the group consisting of hydrogen, halogen, $NH_2$, CN, SH, $CF_3$, $OR^9$, hydrocarbyl, and substituted hydrocarbyl;
$R^8$ is selected from the group consisting of hydrogen and hydroxy; and
$R^9$ is selected from the group consisting of hydrogen, hydrocarbyl, substituted hydrocarbyl, and hydroxy protecting group.

Other aspects and features of the invention will be in part apparent and in part pointed out hereinafter.

DETAILED DESCRIPTION OF THE INVENTION

The present invention provides a process for the selective conversion of 6-keto morphinans to 6-beta-hydroxy morphinans, salts, intermediates, and analogs thereof. It has been discovered that contacting the heterogeneous reaction mixture formed during the reduction of a 6-keto morphinan compound in a concentrated reaction mixture with additional proton acceptor leads to the formation of a homogeneous reaction mixture, wherein the rest of the 6-keto compound may be converted to the 6-hydroxy morphinan compound. Surprisingly, addition of all of the proton acceptor at the start of the reaction or before the reaction becomes heterogeneous results in lower yields, less stereoselective conversion, and increased impurities. As detailed in the Examples, this process produces high yields of the beta isomer.

(I) Process for Preparing 6-Beta-Hydroxy Morphinan Derivatives

Provided herein is a process for preparing 6-beta-hydroxy morphinan compounds. The process comprises two sequential steps. The first step comprises contacting the starting 6-keto morphinan compound with a reducing agent and a first proton acceptor to form a first homogeneous reaction mixture, wherein some of the 6-keto compound is converted to the corresponding 6-hydroxy morphinan compound until a substantially heterogeneous reaction mixture is formed. The second step of the process comprises contacting the heterogeneous reaction mixture with a second proton acceptor to form a second homogeneous reaction mixture, wherein the 6-keto morphinan compound that was not converted to the 6-hydroxy morphinan compound in the first step is converted to the 6-hydroxy morphinan compound. The predominant isomer of the 6-hydroxy morphinan compound is the 6-beta-hydroxy epimer.

For the purposes of discussion, the ring atoms of a morphinan compound are numbered as diagrammed below. Morphinan compounds have asymmetric centers. In particular, the core morphinan compound may have fur chiral carbons; namely, C-5, C-13, C-14, and C-9.

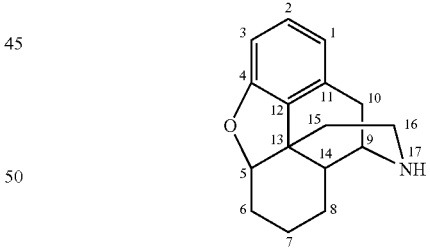

(a) Preparation of 6-beta-hydroxy Morphinan Derivative Comprising Formula (II)

A first aspect of the present invention is the provision of a process for the conversion of a 6-keto morphinan compound comprising Formula (I) to a 6-hydroxy morphinan compound comprising Formula (II). For the purposes of illustration, Reaction Scheme 1 depicts the formation of the 6-hydroxy morphinan compound comprising Formula (II) according to one aspect of the invention:

Reaction Scheme 1:

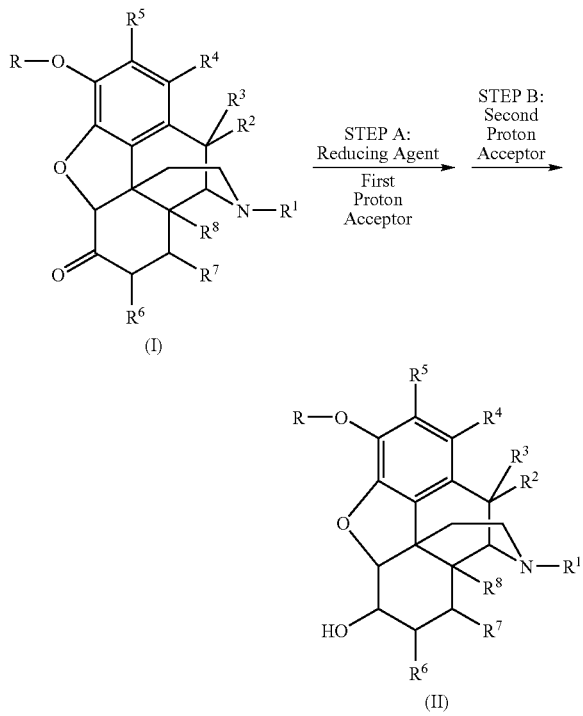

wherein:
R is selected from the group consisting of hydrogen, hydrocarbyl, substituted hydrocarbyl, and hydroxy protecting group
$R^1$ is selected from the group consisting of hydrogen, hydrocarbyl, and substituted hydrocarbyl;
$R^2$ and $R^3$ are independently selected from the group consisting of hydrogen, OH, $NH_2$, SH, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group selected from the group consisting of cycloalkyl ketal, cycloalkyl thiol ketal, and cycloalkyl dithiol ketal;
$R^4$, $R^5$, $R^6$, and $R^7$ are independently selected from the group consisting of hydrogen, halogen, $NH_2$, CN, SH, $CF_3$, $OR^9$, hydrocarbyl, and substituted hydrocarbyl;
$R^8$ is selected from the group consisting of hydrogen and hydroxy; and
$R^9$ is selected from the group consisting of hydrogen, hydrocarbyl, substituted hydrocarbyl, and hydroxy protecting group.

In a preferred iteration, the constituents of the reaction comprise:
R is selected from the group consisting of hydrogen, alkyl, and methyl;
$R^1$ is selected from the group consisting of hydrogen, alkyl, cycloalkyl, alkenyl, aryl, benzyl, and $C(O)_nR^{10}$;
$R^2$, $R^3$, $R^4$, $R^5$, and $R^7$ are each hydrogen;
$R^6$ is selected from the group consisting of H, Br, Cl, F, OH, O-methyl, and O-benzyl;
$R^{10}$ is selected from the group consisting of alkyl and aryl; and
n is an integer from 1 to 2.

The optical activity, with respect to the rotation of polarized light, of a 6-keto morphinan corresponding to Formula (I) may be (+) or (−). Furthermore, the configuration of the chiral carbons, C-5, C-13, C-14, and C-9, respectively, of the compound may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face or the beta face of the molecule.

The optical activity of a 6-hydroxy morphinan corresponding to Formula (II) may be (+) or (−), and the configuration of the chiral carbons, C-6, C-5, C-13, C-14, and C-9, respectively, may be RRRRR, RRRRS, RRSRR, RRSRS, RRRSR, RRRSS, RRSSR, RRSSS, RSRRR, RSRRS, RSSRR, RSSRS, RSRSR, RSRSS, RSSSR, RSSSS, SRRRR, SRRRS, SRSRR, SRSRS, SRRSR, SRRSS, SRSSR, SRSSS, SSRRR, SSRRS, SSSRR, SSSRS, SSRSR, SSRSS, SSSSR, or SSSSS, provided that the C-15 and the C-16 carbons are both either on the alpha face of the molecule or the beta face of the molecule, and the 6-hydroxy is on the beta face of the molecule.

(b) Preparation of 6-beta-hydroxy Morphinan Derivative Comprising Formula (IV)

Another aspect of the present invention provides of a process for the conversion of a 6-keto morphinan compound comprising Formula (III) to a 6-hydroxy morphinan compound comprising Formula (IV). For the purposes of illustration, Reaction Scheme 2 depicts the formation of the 6-hydroxy morphinan compound comprising Formula (IV) according to one aspect of the invention:

Reaction Scheme 2:

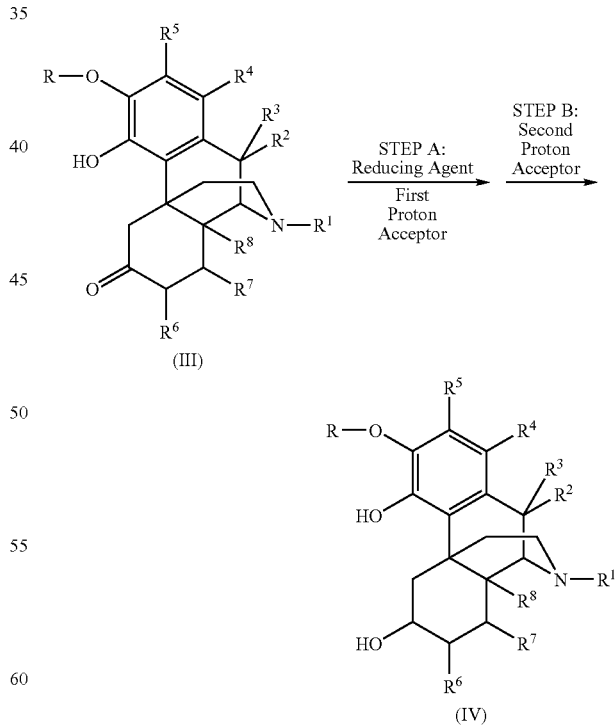

wherein:
R is selected from the group consisting of hydrogen, hydrocarbyl, substituted hydrocarbyl, and hydroxy protecting group $R^1$ is selected from the group consisting of hydrogen, hydrocarbyl, and substituted hydrocarbyl;

$R^2$ and $R^3$ are independently selected from the group consisting of hydrogen, OH, $NH_2$, SH, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group selected from the group consisting of cycloalkyl ketal, cycloalkyl thiol ketal, and cycloalkyl dithiol ketal;

$R^4$, $R^5$, $R^6$, and $R^7$ are independently selected from the group consisting of hydrogen, halogen, $NH_2$, CN, SH, $CF_3$, $OR^9$, hydrocarbyl, and substituted hydrocarbyl;

$R^8$ is selected from the group consisting of hydrogen and hydroxy; and $R^9$ is selected from the group consisting of hydrogen, hydrocarbyl, substituted hydrocarbyl, and hydroxy protecting group.

In a preferred iteration, the constituents of the reaction comprise:

R is selected from the group consisting of hydrogen, alkyl, and methyl;

$R^1$ is selected from the group consisting of hydrogen, alkyl, cycloalkyl, alkenyl, aryl, benzyl, and $C(O)_n R^{10}$;

$R^2$, $R^3$, $R^4$, $R^5$, and $R^7$ are each hydrogen;

$R^6$ is selected from the group consisting of H, Br, Cl, F, OH, O-methyl, and O-benzyl;

$R^{10}$ is selected from the group consisting of alkyl, alkenyl, and aryl; and n is an integer from 1 to 2.

The optical activity of a 6-keto morphinan corresponding to Formula (III) may be (+) or (−). Furthermore, the configuration of the chiral carbons, C-13, C-14, and C-9, respectively, of the compound may be RRR, RRS, RSR, RSS, SRR, SRS, SSR, or SSS, provided that the C-15 and the C-16 carbons are both either on the alpha face or the beta face of the molecule.

The optical activity of a 6-hydroxy morphinan corresponding to Formula (IV) may be (+) or (−), and the configuration of the chiral carbons, C-6, C-13, C-14, and C-9, respectively, may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face or the beta face of the molecule, and the 6-hydroxy is on the beta face of the molecule.

(c) Step A: Contact with a Reducing Agent and a First Proton Acceptor

Step A of the process comprises contacting the 6-keto morphinan compound (I) with a reducing agent and a first proton acceptor to form a first homogeneous reaction mixture. In general, the reducing agent will be an agent for use in a chemical reduction. Suitable reducing agents for the stereoselective reduction of the 6-keto morphinan derivative include sulfinic acids (e.g., formamidine sulfinic acid, hydroxymethane sulfinic acid, and the like); organic compounds having thiol or disulfide groups; reductive inorganic alkali metal and ammonium salts of sulfur-containing acids (e.g., sodium sulfite, disulfite, thiosulfate, hydrosulfite, acetone bisulfite, bisulfite salts, sulfide, hydrosulfide, dithionite salts, and so forth); and combinations of a metal (e.g., tin, zinc, or iron, and so forth) or a metal compound (e.g., chromium chloride, chromium acetate, and the like) with an organic or inorganic acid (e.g., acetic acid, ascorbic acid, formic acid, propionic acid, trifluoroacetic acid, p-toluenesulfonic acid, hydrochloric acid, and the like). In a preferred embodiment, the reducing agent may be a sulfinic acid. In an exemplary embodiment, the sulfinic acid may be formamidine sulfinic acid.

The amount of reducing agent contacted with the 6-keto morphinan compound can and will vary. Typically, the molar/molar ratio of the 6-keto morphinan compound to the reducing agent may range from 1:2 to about 1:8. In a preferred embodiment, the molar/molar ratio of the 6-keto morphinan compound to the reducing agent may range from 1:3 to about 1:5. In an exemplary embodiment, the molar/molar ratio of the 6-keto morphinan compound to the reducing agent may be about 1:4.

In general, the first proton acceptor will have a pKa of greater than about 10.0. Non-limiting examples of suitable proton acceptors include hydroxides of alkali metals and alkaline earth metals (such as, for example, NaOH, KOH, $Ca(OH)_2$ and the like), carbonate salts (such as, for example, $Na_2CO_3$, $K_2CO_3$, $Li_2CO_3$, and the like), borate salts (such as, for example, $Na_2B_4O_7$), di- and tri-basic phosphate salts (such as, for example, $Na_2HPO_4$ and $Na_3PO_4$, and the like), bicarbonate salts (such as, for example, $NaHCO_3$, $KHCO_3$, $LiHCO_3$, and the like), and mixtures of any of the above. In a preferred embodiment, the proton acceptor may be NaOH, KOH, $Na_2CO_3$, or $K_2CO_3$. In an exemplary embodiment, the proton acceptor may be NaOH.

The amount of first proton acceptor contacted with the 6-keto morphinan compound can and will vary. The molar/molar ratio of the 6-keto morphinan compound to the first proton acceptor may range from about 1:2 to about 1:11. In a preferred embodiment, the molar/molar ratio of the 6-keto morphinan compound to the first proton acceptor may range from about 1:3 to about 1:9. In an exemplary embodiment, the molar/molar ratio of the 6-keto morphinan compound to the first proton acceptor may be about 1:4.

The reaction is typically conducted in the presence of a solvent. In general, the choice of a solvent will depend upon the solubility of the morphinan compounds. Accordingly, the solvent may be a protic solvent, an aprotic solvent, or a combination thereof. Non-limiting examples of suitable protic solvents include, water, an aqueous solution (such as, e.g., a dilute acid, a dilute base, a simple salt solution, a buffered solution, etc.), a lower chain alcohol (such as methanol, ethanol, and the like), and combinations thereof. Non-limiting examples of aprotic solvents include ether solvents, acetone, acetonitrile, benzene, dimethylformamide (DMF), dimethyl sulfoxide (DMSO), N,N-dimethylpropionamide, 1,3-dimethyl-3,4,5,6-tetrahydro-2(1H)-pyrimidinone, 1,3-dimethyl-2-imidazolidinone, 1,2-dimethoxyethane, N,N-dimethylacetamide, N-methylpyrrolidinone, ethyl acetate, ethyl formate, ethyl methyl ketone, formamide, hexamethylphosphoramide, methyl acetate, N-methylacetamide, N-methylformamide, methylene chloride, nitrobenzene, nitromethane, propionitrile, sulfolane, tetramethylurea, tetrahydrofuran, toluene, trichloromethane, and combinations thereof. In a preferred embodiment, the solvent may be a protic solvent. In an exemplary embodiment, the protic solvent may be water.

The volume of solvent added to the reactants can and will vary depending upon the embodiment. In general, the amount of solvent will be less that about 40 liters per kilogram of starting material. In a preferred embodiment, the volume of solvent contacted with the 6-keto morphinan compound may range from about 8 liters to about 20 liters of solvent per kilogram of 6-keto morphinan compound. In another preferred embodiment, the volume of solvent contacted with the 6-keto morphinan compound may range from about 9 liters to about 16 liters of solvent per kilogram of 6-keto morphinan compound. In an exemplary embodiment, the volume of solvent contacted with the 6-keto morphinan compound may be about 10 liters per kilogram of 6-keto morphinan compound.

The reaction generally is conducted at a temperature that ranges from about 20° C. to about 75° C. In a preferred embodiment, the temperature of the reaction may range from about 50° C. to about 70° C. In another preferred embodiment, the temperature of the reaction may be about 60° C. In an exemplary embodiment, the temperature of the reaction may be about 65° C. The reaction is preferably performed under ambient pressure, and preferably in an inert atmosphere (e.g., nitrogen or argon).

Typically, the reaction is allowed to proceed until the reaction mixture becomes substantially heterogeneous. In the context of the present invention, a heterogeneous reaction mixture comprises a solid phase and a liquid phase. The physical state of the reaction mixture may be monitored visually or spectrophotometrically. In general, the reaction is substantially heterogeneous when no additional solid phase is formed. When the reaction mixture is substantially heterogeneous, the reaction stalls and the conversion of the 6-keto compound to the 6-hydroxy compound essentially stops. As used herein, the term "stall" refers to a reaction in which the conversion stops completely or slows to such a slow rate that it is essentially stopped.

Prior to the stalling of the reaction in Step A, however, typically at least about 40% of the 6-keto compound is converted to the 6-hydroxy compound. In one embodiment, at least about 50% of the 6-keto compound may be converted to the 6-hydroxy compound during Step A. In another embodiment, at least about 60% of the 6-keto compound may be converted to the 6-hydroxy compound during Step A. In still another embodiment, at least about 70% of the 6-keto compound may be converted to the 6-hydroxy compound during Step A. In an alternate embodiment, at least about 80% of the 6-keto compound may be converted to the 6-hydroxy compound during Step A. In another alternate embodiment, at least about 90% of the 6-keto compound may be converted to the 6-hydroxy compound during Step A. The conversion of the 6-keto compound to the 6-hydroxy compound may be determined using a standard technique, such as chromatography (e.g., HPLC).

(d) Step B: Contact with a Second Proton Acceptor

Step B of the process comprises adding a second proton acceptor to the substantially heterogeneous reaction mixture, wherein a second homogeneous reaction mixture is formed and the 6-keto compound that was not converted to the 6-hydroxy compound in Step A is converted to the 6-hydroxy compound. In general, the second proton acceptor will have a pKa of greater than about 10.0. Suitable proton acceptors are presented above in (II)(c). The identity of the second proton acceptor used in Step B may be the same as that of the first proton acceptor used in Step A. Alternatively, the identity of the second proton acceptor may be different from that of the first proton acceptor. In a preferred embodiment, the second proton acceptor may be sodium hydroxide.

The molar/molar ratio of the 6-keto compound to the second proton acceptor may range from about 1:0.5 to about 1:2. Preferably, the molar/molar ratio of the 6-keto compound to the second proton acceptor may be about 1:1. Stated another way, the molar/molar ratio of the first proton acceptor to the second proton acceptor may range from about 3:1 to about 15:1, or more preferably about 7:1. In general, the second proton acceptor is added in a volume such that the total volume of the reaction mixture increases by no more that about 20%. In some embodiments, the volume of the reaction increases by less that 20%, less than about 15%, less than about 10%, less than about 5%, less than about 2%, or less than about 1%.

Without being bound by any particular theory, it appears that addition of the second proton acceptor creates an oversaturation of the 6-keto compound, wherein the reaction mixture becomes homogeneous. Formation of a homogeneous reaction, therefore, allows for the conversion of the unreacted 6-keto compound to the 6-hydroxy compound. The reaction is conducted at a temperature and conditions as detailed above. Typically, the reaction is allowed to proceed for a sufficient period of time until the reaction is complete, as determined using a standard technique. In this context, a "completed reaction" generally means that the reaction mixture contains a significantly diminished amount of the starting material (i.e., the 6-keto morphinan compound) and a significantly increased amount of the product (i.e., the 6-hydroxy morphinan compound) compared to the amounts of each present at the beginning of the reaction.

The yield of 6-hydroxy morphinan product may vary depending on the compound being synthesized. Typically, the yield of the product may be at least about 70%. Stated another way, at least about 70% of the 6-keto compound may be converted to the 6-hydroxy compound during both Steps A and B of the reaction. In one embodiment, at least about 80% of the 6-keto compound may be converted to the 6-hydroxy compound during Steps A and B. In another embodiment, at least about 90% of the 6-keto compound may be converted to the 6-hydroxy compound during Steps A and B. In still another embodiment, at least about 95% of the 6-keto compound may be converted to the 6-hydroxy compound during Steps A and B.

The product of the reaction may comprise a mixture of 6-beta-hydroxy and 6-alpha-hydroxy epimers. Typically, the epimeric ratio of 6-beta-hydroxy to 6-alpha-hydroxy will be at least about 4:1. In one embodiment, the epimeric ratio of 6-beta-hydroxy to 6-alpha-hydroxy may be at least about 20:1. In another embodiment, the epimeric ratio of 6-beta-hydroxy to 6-alpha-hydroxy may be at least about 50:1. In still another embodiment, the epimeric ratio of 6-beta-hydroxy to 6-alpha-hydroxy may be at least about 99:1.

(e) Exemplary Embodiment

In an exemplary embodiment, the reducing agent is formamidine sulfinic acid, the first and second proton acceptors are sodium hydroxide, and the protic solvent is water. The molar ratios of 6-keto morphinan compound to reducing agent to first proton acceptor to second proton acceptor may be 1:4:7:1, wherein about 10 liters of protic solvent is used per kilogram of 6-keto morphinan compound. The reaction is conducted at a temperature of about 65° C. under an inert atmosphere.

(II) Compounds Prepared from 6-Beta-Hydroxy Morphinans

The process for the conversion of the 6-keto group to the 6-beta-hydroxy group may yield an end product morphinan or an intermediate morphinan, which may be modified in one or more additional steps to achieve the desired end compound. Furthermore, the conversion of a 6-keto morphinan to the corresponding 6-beta-hydroxy morphinan may occur at any step of the overall process in the preparation of the desired morphinan. For example, the reduction of the 6-keto group may occur before or after alkylation (or other modification) of the morphinan nitrogen.

Exemplary 6-beta-hydroxy morphinan compounds having Formula (II) include nalbuphine, oxymorphol, oxycodol, noroxymorphol, naloxol, naltrexol, hydrocodol, and hydromorphol:

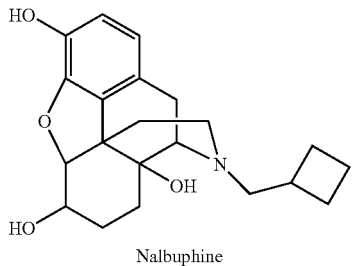
Nalbuphine

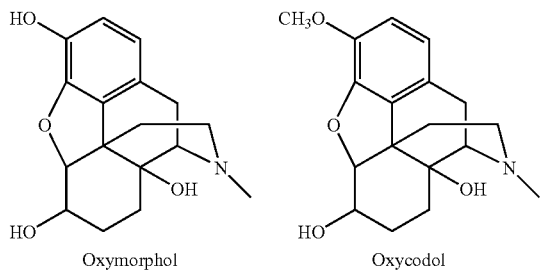
Oxymorphol        Oxycodol

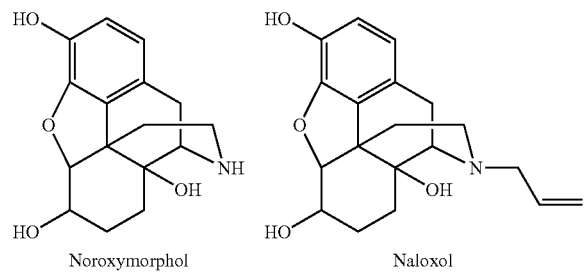
Noroxymorphol        Naloxol

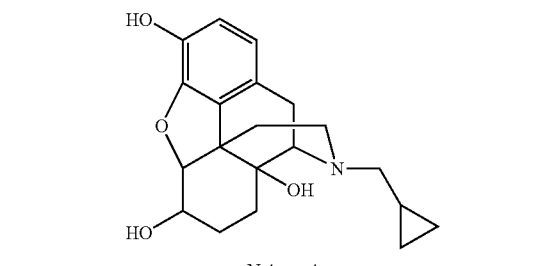
Naltrexol

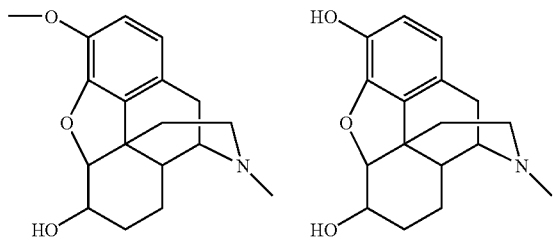
Hydrocodol        Hydromorphol

DEFINITIONS

The compounds described herein may have asymmetric centers. Compounds containing an asymmetrically substituted atom may be isolated in optically active or racemic form. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R_1$, $R_1O$—, $R_1R_2N$—, or $R_1S$—, $R_1$ is hydrocarbyl, heterosubstituted hydrocarbyl, or heterocyclo, and $R_2$ is hydrogen, hydrocarbyl or substituted hydrocarbyl.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "homogeneous reaction" as used herein refers to a reaction in which the reactants are in the same phase (e.g., all of the reactants are liquids, all of the reactants are gases, etc.). The term "heterogeneous reaction" refers to a reaction in which the reactants are in two or more phases.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "hydroxy protecting group" as used herein denote a group capable of protecting a free hydroxy group ("protected hydroxy") which, subsequent to the reaction for which protection is employed, may be removed without disturbing the remainder of the molecule. Exemplary hydroxy protecting groups include oxygen protecting groups of alkylsulfonates and arylsulfonates, ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilyiethyl carbonate), silyl ethers (e.g., trimethylsilyl (TMS), triethylsilyl (TES), triisopropylsilyl (TIPS), triphenyisilyl (TPS), t-butyldimethylsilyl (TBDMS), t-butyldiphenylsilyl (TBDPS) and the like. A variety of protecting groups for the hydroxy group and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds and processes without departing from the scope of the invention, it is intended that all matter contained in the above description and in the examples given below, shall be interpreted as illustrative and not in a limiting sense.

The following examples are included to demonstrate preferred embodiments of the invention. It should be appreciated by those of skill in the art that the techniques disclosed in the following examples represent techniques discovered by the inventors to function well in the practice of the invention. Those of skill in the art should, however, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

EXAMPLES

The following examples illustrate various embodiments of the invention.

Example 1

Preparation of 6-Beta-Oxymorphol by Reduction of Oxymorphone

The synthesis of 6-beta-oxymorphol is depicted in the following scheme:

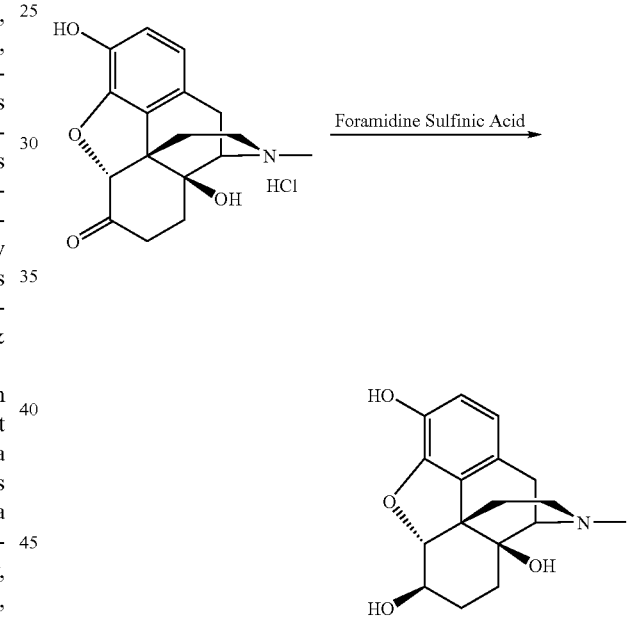

1.00 gram of oxymorphone HCl and 1.28 grams of formamidine sulfinic acid (4 equivalents) were added to a three-neck flask that was equipped with a stirrer, a heating apparatus, and a nitrogen source. 10.0 mL of an aqueous solution of 2N NaOH was then added under nitrogen protection. The stirrer is turned on and the mixture was heated to 65° C. The reaction was run for 2 hours at this temperature, wherein the mixture formed a white slurry. After 1 mL of an aqueous solution of 3N NaOH was added to the slurry, a clear solution was produced. The reaction was kept at this temperature for another 2 hours and then cooled. The pH of the reaction solution was adjusted to 10-10.5 using an aqueous solution of saturated NH$_4$Cl. The product precipitated as a white solid and was separated by filtration. The conversion rate was typically greater than 98% at this point. The recovery was typically great than 95%. The stereoselectivity of the beta isomer was about 95:5.

Example 2

Preparation of 6-Beta-Naltrexol by Reduction of Naltrexone

The synthesis of 6-beta-naltrexol is depicted in the following scheme:

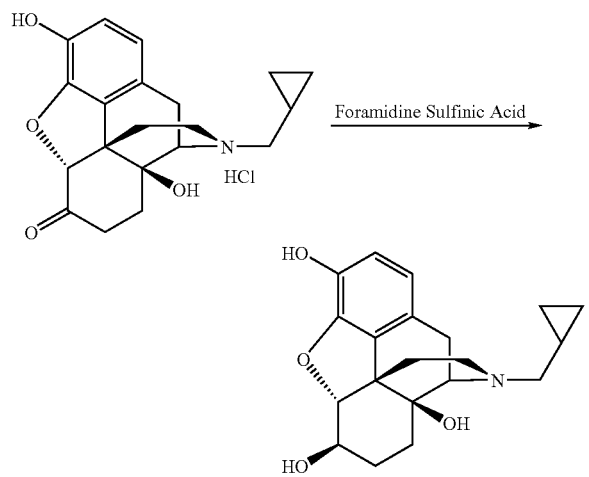

1.00 gram of naltrexone HCl and 1.07 grams of foramidine sulfinic acid (4 equivalents) were added to a three-neck flask that was equipped with a stirrer, a heating apparatus, and a nitrogen source. 10.0 mL of an aqueous solution of 2N NaOH was then added under nitrogen protection. The mixture was stirred and heated to 65° C. The reaction was run for 2 hours at this temperature, wherein the mixture formed a white slurry. After 1 mL of an aqueous solution of 3N NaOH was added to the slurry, a clear solution was formed. The reaction was kept at this temperature for another 2 hours and then cooled. The pH of the reaction solution was adjusted to 10-10.5 using an aqueous solution of saturated NH$_4$Cl. The product precipitated as a white solid and was separated by filtration. The conversion rate was typically greater than 99% at this point. The recovery was typically great than 98%. The stereoselectivity of the beta isomer was about 97:3.

Example 3

Preparation of 6-Beta-Hydroxyl Sinomenine by Reduction of Sinomenine

The synthesis of 6-beta-hydroxyl simomenine is depicted in the following scheme:

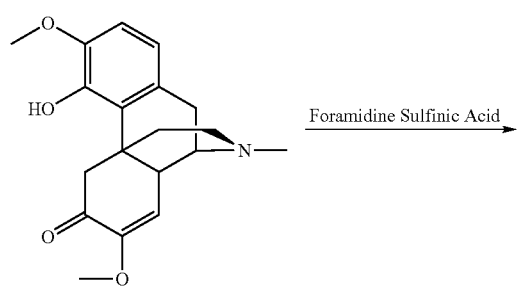

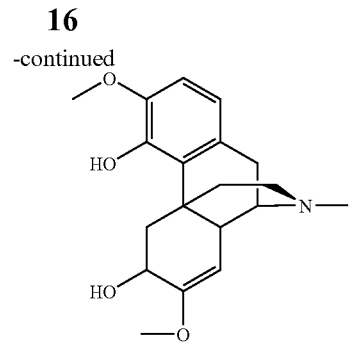

1.00 gram of naltrexone HCl and 1.00 grams of formamidine sulfinic acid (4 equivalents) were added to a three-neck flask that was equipped with a stirrer, a heating apparatus, and a nitrogen source. 10.0 mL of an aqueous solution of 2N NaOH was then added under nitrogen protection. The mixture was stirred and heated to 60° C. The reaction was run for 2 hours at this temperature, wherein the mixture formed a white slurry. After 1 mL of an aqueous solution of 3N NaOH was added to the slurry, a clear solution was formed. The reaction was kept at this temperature for another 2 hours and then cooled. The pH of the reaction solution was adjusted to 10-10.5 using an aqueous solution of saturated NH$_4$Cl. The product precipitated as a white solid and was separated by filtration. The conversion rate was typically greater than 99% at this point. The recovery was typically great than 90%. The stereoselectivity of the beta isomer was about 85:15.

Example 4

Preparation of 6-Beta-Hydroxyl Bromo-Sinomenine Derivative

The synthesis of 6-beta-hydroxyl bromo-simomenine is depicted in the following scheme:

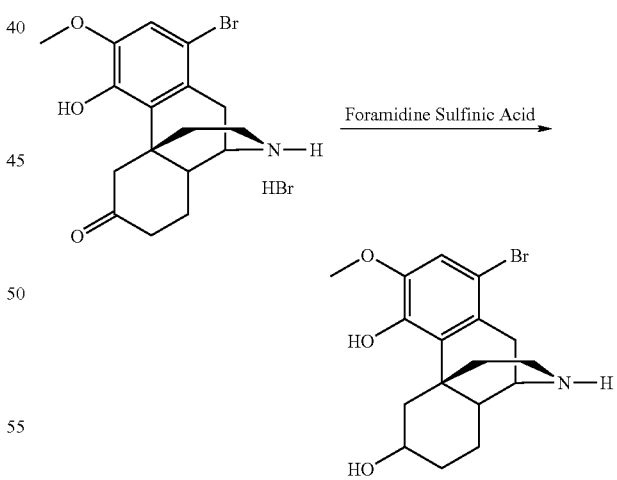

1.03 grams of naltrexone HCl and 1.00 grams of formamidine sulfinic acid (4 equivalents) were added to a three-neck flask that was equipped with a stirrer, a heating apparatus, and a nitrogen source. 10.0 mL of an aqueous solution of 2N NaOH was then added under nitrogen protection. The mixture was stirred and heated to 60° C. The reaction was run for 2 hours at this temperature, wherein the mixture formed a white slurry. After 1 mL of an aqueous solution of 3N NaOH was added to the slurry, a clear solution was formed. The reaction was kept at this temperature for another 2 hours and then cooled. The pH of the reaction solution was adjusted to 10-10.5 using an aqueous solution of saturated NH₄Cl. The product precipitated as a white solid and was separated by filtration. The conversion rate was typically greater than 90% at this point. The recovery was typically great than 85%. The stereoselectivity of the beta isomer was about 80:20.

Example 5

Preparation of (+)-β-Naltrexol (+)-β-Naltrexol was prepared from (+)-naltrexone according to the following reaction scheme:

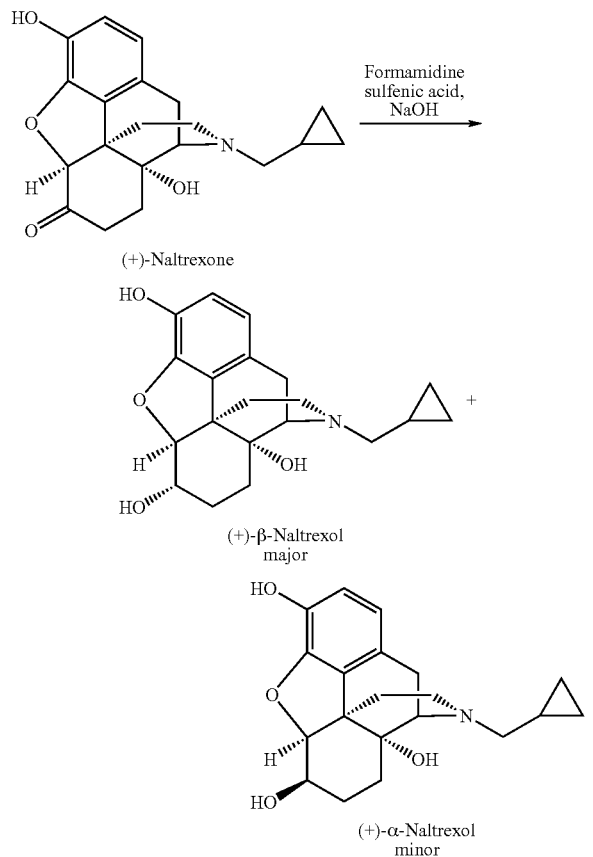

(+)-Naltrexone (250 mgs) was suspended in water (3 mL). The solution was purged with nitrogen with stirring and then kept under a nitrogen atmosphere. Formamidine sulfenic acid (1.0 g) was added. A drop of 4N sodium hydroxide (NaOH) was added for dissolution of the reactants. The reaction was stirred at room temperature for 30 min and then heated to 60° C. for 3 h. HPLC analysis indicated that the reaction was complete. Water (15 mL) was added. The pH was adjusted with glacial acetic acid until pH=9 to 10. The aqueous contents were extracted with chloroform (3×10 mL). The combined chloroform layers were washed with water (2×5 mL). The volatile solvents were removed under reduced pressure with mild heating. (+)-β-Naltrexol (100 mgs) were recovered as an off-white solid.

Example 6

Preparation of (+)-β-Naloxol (+)-β-Naloxol was prepared from (+)-naloxone according to the following reaction scheme:

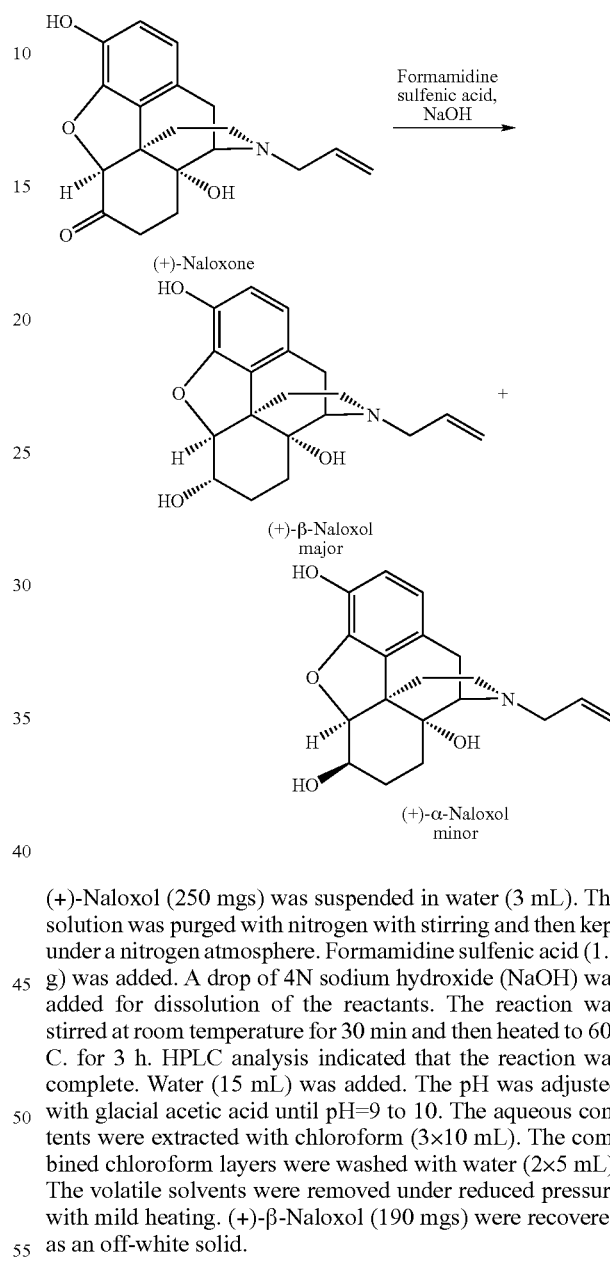

(+)-Naloxol (250 mgs) was suspended in water (3 mL). The solution was purged with nitrogen with stirring and then kept under a nitrogen atmosphere. Formamidine sulfenic acid (1.0 g) was added. A drop of 4N sodium hydroxide (NaOH) was added for dissolution of the reactants. The reaction was stirred at room temperature for 30 min and then heated to 60° C. for 3 h. HPLC analysis indicated that the reaction was complete. Water (15 mL) was added. The pH was adjusted with glacial acetic acid until pH=9 to 10. The aqueous contents were extracted with chloroform (3×10 mL). The combined chloroform layers were washed with water (2×5 mL). The volatile solvents were removed under reduced pressure with mild heating. (+)-β-Naloxol (190 mgs) were recovered as an off-white solid.

What is claimed is:

1. A process for preparing a compound, the process comprising:
  (a) contacting a 6-keto morphinan compound comprising Formula (I) with a reducing agent, a first proton acceptor and a solvent, wherein the concentration of the 6-keto morphinan of Formula (I) in the solvent is at least 25 grams per liter, to form a first homogeneous reaction mixture, wherein some of compound (I) is converted to a 6-hydroxy morphinan compound comprising Formula (II) to produce a substantially heterogeneous reaction mixture; and (b) contacting the heterogeneous reaction mixture with a second proton acceptor to form a second homogeneous reaction mixture, wherein some of compound (I) that was not converted to compound (II) in step (a) is converted to compound (II), the process of steps (a) and (b) proceeding according to the reaction scheme:

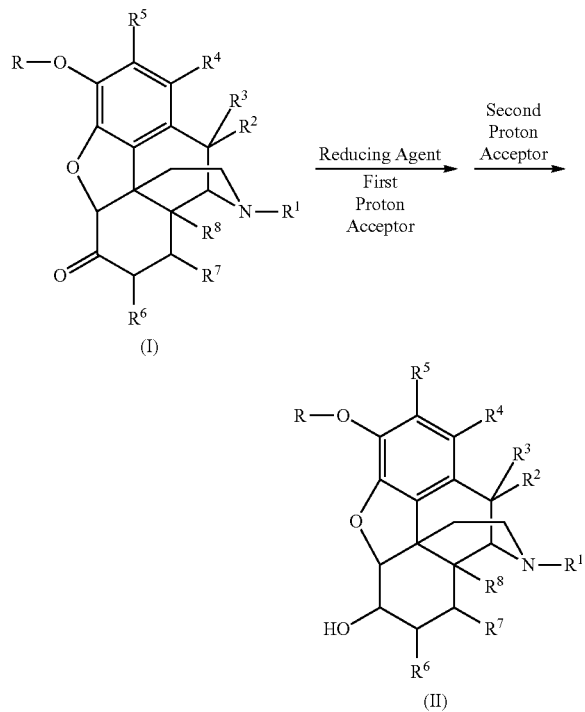

wherein:
- R is chosen from hydrogen, hydrocarbyl, substituted hydrocarbyl and hydroxy protecting group;
- $R^1$ is chosen from hydrogen, hydrocarbyl, and substituted hydrocarbyl;
- $R^2$ and $R^3$ are independently chosen from hydrogen, OH, $NH_2$, SH, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group chosen from cycloalkyl ketal, cycloalkyl thiol ketal, and cycloalkyl dithiol ketal;
- $R^4$, $R^5$, $R^6$, and $R^7$ are independently chosen from hydrogen, halogen, $NH_2$, CN, SH, $CF_3$, $OR^9$, hydrocarbyl, and substituted hydrocarbyl;
- $R^8$ is chosen from hydrogen and hydroxy; and
- $R^9$ is chosen from hydrogen, hydrocarbyl, substituted hydrocarbyl, and hydroxy protecting group.

2. The process of claim 1, wherein:
- R is chosen from hydrogen, alkyl, and methyl;
- $R^1$ is chosen from hydrogen, alkyl, cycloalkyl, alkenyl, aryl, benzyl, and $C(O)_n R^{10-}$;
- $R^2$, $R^3$, $R^4$, $R^5$, and $R^7$ are each hydrogen;
- $R^6$ is chosen from H, Br, Cl, F, OH, O-methyl, and O-benzyl;
- $R^{10}$ is chosen from alkyl, alkenyl, and aryl; and
- n is an integer from 1 to 2.

3. The process of claim 1, wherein the 6-hydroxy morphinan compound (II) is a mixture of 6-alpha-hydroxy and 6-beta-hydroxy morphinan epimers.

4. The process of claim 3, wherein the epimeric ratio of 6-beta-hydroxy to 6-alpha-hydroxy morphinan epimers is chosen from at least 4:1, at least 50:1, and at least about 99:1.

5. The process of claim 1, wherein the reducing agent is a sulfinic acid chosen from formamidine sulfinic acid and hydroxymethane sulfinic acid; and the first proton acceptor and the second proton acceptor are independently chosen from sodium hydroxide, potassium hydroxide, potassium carbonate, and sodium bicarbonate.

6. The process of claim 1, wherein the molar/molar ratio of compound (I) to reducing agent is from about 1:2 to about 1:8; the molar/molar ratio of compound (I) to the first proton acceptor is from about 1:3 to about 1:11; and the molar/molar ratio of compound (I) to the second proton acceptor is from about 1:0.5 to about 1:2.

7. The process of claim 1, wherein the reaction is conducted in the presence of a protic solvent.

8. The process of claim 1, wherein the reaction is conducted at a temperature ranging from about 20° C. to about 75° C.

9. The process of claim 1, wherein at least about 40% of compound (I) is converted to compound (II) in step (a).

10. The process of claim 1, wherein at least about 70% of compound (I) is converted to compound (II) in both steps (a) and (b).

11. The process of claim 2, wherein the optical activity of compound (I) is (+) or (−), and the configuration of C-5, C-13, C-14, and C-9, respectively, is chosen from RRRR, RRSR, RRRS, RRSS, RSRR, RSSR, RSRS, RSSS, SRRR, SRSR, SRRS, SRSS, SSRR, SSSR, SSRS, and SSSS, provided that the C-15 and the C-16 carbons are both either on the alpha face of the molecule or the beta face of the molecule; and the optical activity of compound (II) is (+) or (−), and the configuration of C-6, C-5, C-13, C-14, and C-9, respectively, is chosen from RRRRR, RRRRS, RRSRR, RRSRS, RRRSR, RRRSS, RRSSR, RRSSS, RSRRR, RSRRS, RSSRR, RSSRS, RSRSR, RSRSS, RSSSR, RSSSS, SRRRR, SRRRS, SRSRR, SRSRS, SRRSR, SRRSS, SRSSR, SRSSS, SSRRR, SSRRS, SSSRR, SSSRS, SSRSR, SSRSS, SSSSR, and SSSSS, provided that the C-15 and the C-16 carbons are both either on the alpha face of the molecule or the beta face of the molecule, and the 6-hydroxy is on the beta face of the molecule.

* * * * *